(12) United States Patent
Rogers

(10) Patent No.: US 6,210,368 B1
(45) Date of Patent: Apr. 3, 2001

(54) RESERVOIR VOLUME SENSORS

(75) Inventor: Charles R. Rogers, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/070,176

(22) Filed: Apr. 30, 1998

(51) Int. Cl.[7] ................................................ A61M 31/00
(52) U.S. Cl. ................................................ 604/131
(58) Field of Search ................................ 604/131, 132, 604/140, 141, 145, 153, 151

(56) References Cited

U.S. PATENT DOCUMENTS

| 3,731,681 | * | 5/1973 | Blackshear et al. | 604/141 |
| 4,360,019 | * | 11/1982 | Portner et al. | 604/131 |
| 4,505,710 | * | 3/1985 | Collins | 604/131 |
| 4,692,147 | | 9/1987 | Duggan . | |
| 5,135,499 | * | 8/1992 | Tafani et al. | 604/140 |
| 5,445,616 | | 8/1995 | Kratoska et al. . | |
| 5,505,706 | * | 4/1996 | Maus et al. | 604/131 |
| 5,569,190 | * | 10/1996 | D'Antonio | 604/72 |
| 5,743,878 | * | 4/1998 | Ross et al. | 604/131 |
| 5,766,150 | * | 6/1998 | Langkau | 604/140 |
| 5,810,015 | * | 9/1998 | Flaherty | 604/131 |

* cited by examiner

*Primary Examiner*—Jeffrey A. Smith
*Assistant Examiner*—Eduardo C. Robert
(74) *Attorney, Agent, or Firm*—Banner & Witcoff, Ltd.

(57) ABSTRACT

Reservoir volume in a drug delivery device is sensed by providing a capacitor, the capacitance of which varies with bellows position or, alternatively, with the amount of propellant liquid absorbed in a dielectric material. In one embodiment, a capacitance is provided between a surface of the bellows, which acts as a first capacitor plate, and a conductive surface disposed proximate the bellows, which acts as a second capacitor plate. As the bellows moves from its extended full position to its collapsed empty position, the area of overlap, and therefore the capacitance between the first and second plates varies from a maximum value to a minimum value. In another embodiment, a variable capacitor is provided with an absorbent material. The absorbent material absorbs the liquid phase of the propellant in the pump housing and acts as a dielectric between two stationary conductive plates provided in the housing. The amount of liquid propellant absorbed in the absorbent material varies with the reservoir volume. When the reservoir is in its full, expanded position, more liquid propellant is absorbed in the absorbent material. When the reservoir is in its compressed empty position, more of the propellant exists as vapor within the pump housing and therefore less liquid propellant is absorbed in the absorbent material. The dielectric properties of the capacitor are therefore higher and the capacitance is therefore maximized when the reservoir is in its full, extended position. Conversely, the dielectric properties are lower and the capacitance minimized when the reservoir is in its compact, empty position.

31 Claims, 2 Drawing Sheets

RESERVOIR VOLUME SENSORS

FIELD OF THE INVENTION

This invention relates to sensing devices and methods of sensing. This invention also relates to capacitors in general. Particularly, the invention relates to apparatus and methods for sensing the volume of drug in a drug delivery device using capacitance.

BACKGROUND OF THE INVENTION

Drug delivery devices are well known and used widely in the treatment of patients. One form of such delivery devices is an implantable infusion pump which typically includes an expansible reservoir for containing a refillable supply of drug. Flow control and refill features are also provided on the pump. Pumps of this type are disclosed in U.S. Pat. Nos. 4,692,147 to Duggan and 5,445,616 to Kratoska et al, the subject matter of which is incorporated herein by reference. State-of-the-art pumps typically contain a propellant that exists in liquid and vapor phases to maintain a constant vapor pressure on the drug reservoir, which is typically an expansible metal bellows. The vapor pressure of the propellant remains substantially constant as the volume of the bellows and therefore the volume of the space between the bellows and pump housing changes.

Frequently, throughout the life and use of a drug delivery device, it is advantageous to periodically determine the volume of drug contained in the drug reservoir. For example, when an implantable pump is refilled, it is beneficial for a physician or technician to know the precise volume of drug remaining in the reservoir and to detect when the pump has been completely refilled. Likewise, periodic volume readings during pump operation permit a physician or possibly even a patient to determine when refilling should be scheduled. Such volume data can also be used to determine or possibly predict pump or infusion system malfunctions or leaks.

Prior art techniques for determining reservoir volume tend to rely on labor and time intensive methods. For example, during refill, the residual supply of drug in the pump may be determined by evacuating, to the extent possible, the residual supply of drug in the pump. Given the amount of effort and time involved in known techniques, it would be advantageous to provide a device for quickly, easily and accurately sensing the volume of drug contained in the reservoir at any desired time.

SUMMARY OF THE INVENTION

The invention reveals a unique discovery: the concept of determining reservoir volume by measuring capacitance associated with component features of a delivery device. One aspect of the invention provides capacitance that varies dependent on the position of a bellows reservoir. Another aspect provides capacitance that varies dependent on the amount of propellant liquid within the delivery device housing. The amount of propellant liquid in the device housing varies with the reservoir volume because propellant liquid evaporates as the reservoir volume decreases. The invention provides volume-sensing capabilities without increase in volume or size of a delivery device. It also provides compatibility with Magnetic Resonance Imaging techniques and offers low power consumption. Still further, the invention provides reservoir volume sensing that compensates for asymmetrical positioning of a bellows reservoir.

According to a preferred embodiment, a capacitance is provided between an outer surface of a bellows reservoir, which acts as a first capacitor plate, and a conductive surface disposed proximate the bellows, which acts as a second capacitor plate. Preferably, the surface is provided on a conductive ring which surrounds the bellows. The ring is supported within the pump housing on insulated spacers. As the bellows moves from its extended full position to its collapsed empty position, the area of overlap, and therefore the capacitance between the first and second plates varies from a maximum value to a minimum value. An absorbent material is provided as a wick to absorb any liquid propellant in the pump housing to thereby prevent liquid propellant from affecting the capacitance between the bellows and the conductive ring.

According to another aspect and preferred embodiment of the invention, a variable capacitor is provided with an absorbent material as a dielectric. The absorbent material is provided to absorb the liquid phase of the propellant in the pump housing and acts as a dielectric, having variable dielectric properties, between two stationary conductive plates provided in the housing. The amount of liquid propellant absorbed in the absorbent material varies with the reservoir volume. When the reservoir is in its full, expanded position, more liquid propellant is absorbed in the absorbent material. When the reservoir is in its compressed empty position, more of the propellant exists as vapor within the pump housing and therefore less liquid propellant is absorbed in the absorbent material. The dielectric properties of the capacitor are therefore higher and the capacitance is therefore maximized when the reservoir is in its full, extended position. Conversely, the dielectric properties are lower and the capacitance minimized when the reservoir is in its compact, empty position.

The objects, advantages novel features, and the further scope of applicability of the present invention will be set forth in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings, in which like numbers refer to like parts throughout.

DESCRIPTION OF THE PREFERRED EMBODIMENTS

Figure 1:
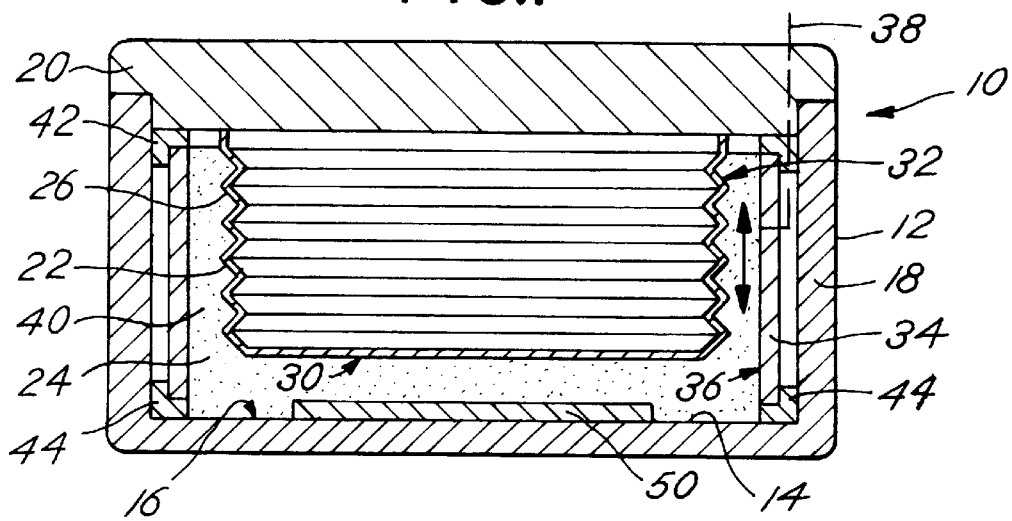
FIG. 1 is a cross-section of a delivery device incorporating a volume sensing device according to a preferred embodiment of the invention.

Referring the FIG. 1, a reservoir volume sensing device according to a preferred embodiment is illustrated in cross-section. Those skilled in the art will recognize that FIG. 1 is a cross-section of a generally circular pump 10 which includes a circular housing 12 having a bottom 14, upper surface 16 of bottom 14 and side wall 18. Bulkhead 20 is provided with a number of refill and flow control features (none shown) a description of which is not necessary for an understanding of the invention. Bulkhead 20 is sealingly fastened to housing 12 to define an inner chamber. Bulkhead 20 and housing 12 may be constructed of any biocompatible material such as titanium.

An expansible bellows reservoir 22 is disposed within the inner chamber and sealingly secured to bulkhead 20 to define therewith a drug-containing space. Bellows reservoir 22 is constructed of a deformable material, such as titanium and includes a plurality of convolutions 26, a bellows bottom surface 30 and a conductive surface 32. It will be appreciated that bellows 22 may be constructed entirely of a conductive material, or alternatively, mainly of a non-conductive material, i.e., polymer, and provided with a conductive material on its outer surface. Conductive surface 32 is in electrical communication with bulkhead 20 which has conductive properties so as to permit electrical charge on conductive surface 32 to be communicated to pump bulkhead 20. The exterior of bellows 22 defines a space with housing 12 in which a propellant (not shown) is provided for maintaining a substantially constant pressure on bellows 22. Bellows 22 may assume an expanded, full position as illustrated in FIGS. 1–5, and, as the drug supply contained therein depletes, a collapsed, empty position in which bellows bottom surface 30 is disposed more proximate bulkhead 20. The general structure described immediately above is characteristic of state-of-the-art implantable pumps.

Referring again to FIG. 1, in accordance with the invention, a capacitor is provided on the pump interior. Capacitance is achieved through a member 34 which may be constructed entirely of a conductive material or may be constructed primarily of a non-conductive material and provided with a conductive surface 36 that is electrically isolated from conductive surface 32 of bellows 22. Member 34 or conductive surface 36 is in electrical communication with a feed through wire, schematically represented by dotted line 38. Feed through wire 38 is electrically isolated from bulkhead 20 and conductive surface 32 of reservoir 22. Member 34 is preferably provided in the form of a metal, i.e, titanium, ring disposed in a surrounding relationship with bellows 22. Member 34 may take other forms, such as a conductive flex circuit described below or a plurality of electrically connected strips disposed around and proximate bellows 22, without departing from the spirit and scope of the invention. Member 34 is held in position with the use of a lower annular spacer 44 and an upper annular spacer 42, both constructed of an insulating material such as plastic or ceramic.

Member 34 may be constructed as a composite flex circuit comprised of a thin conductive sheet laminated between two sheets or films of insulating material. The resulting laminated structure is flexible enough that it may be formed as a generally planar element and then formed into a ring shape without loss of its conductive and insulative properties. Such a flex circuit ring may be formed for a close or contact fit with the outer periphery of bellows 22 such that structural support for the flex circuit ring is provided in part by the bellows 22. Support may also be provided by the upper surface 16 of pump housing bottom and the lower surface of pump bulkhead 20 which may contact the lower and upper edges, respectively, of the flex circuit ring which is sized with an appropriate vertical height. With such a flex circuit construction, upper annular spacer 42 and lower annular spacer 44 may be eliminated.

As will be apparent to those of ordinary skill, the annular convolutions 26 of bellows 22 define a first capacitor plate and member 34 defines a second capacitor plate, electrically isolated from the first capacitor plate and defining therewith a capacitive space 40. The overlapping areas of bellows 22 and member 34 and thus the size of capacitive space 40 varies with the position of bellows reservoir 22. Space 40 is maximized when bellows is in its full, expanded position and minimized when bellows 22 is in its empty, contracted position (not shown). The capacitance may be monitored using basic electrical measurement circuitry by applying a time-dependent voltage across feed through wire 38 and the pump common ground, for example, bulkhead 20. For example, the capacitance may be determined using alternating current and monitoring the impedance characteristics of the capacitive circuit comprised of the aforementioned components.

Still referring to FIG. 1, in accordance with another aspect of the invention, a circular disk of absorbent material 50 is disposed on the upper surface 16 of housing bottom 14 in order to contain any liquid propellant residing within pump housing 12. Containment of liquid propellant is preferred because such liquid may tend to influence the capacitance between bellows 22 and member 34 in the case where liquid, because of changes in implanted pump orientation, may occupy portions of capacitive space 40. Preferably, absorbent material 50 takes the form of a polyvinyl alcohol sponge, although other materials, for example, natural or synthetic felt or cellulose materials may be suitable. It will be recognized that the shape of circular disk may be modified to other suitable forms without departing from the scope of the invention.

Figure 2:
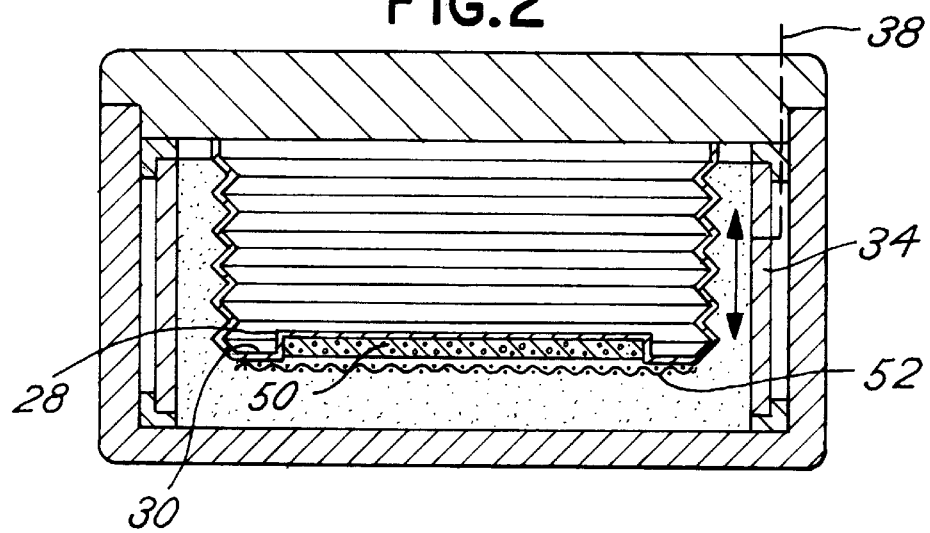
FIG. 2 is a cross-section of a delivery device incorporating a volume sensing device according to another preferred embodiment of the invention.
Figure 3:
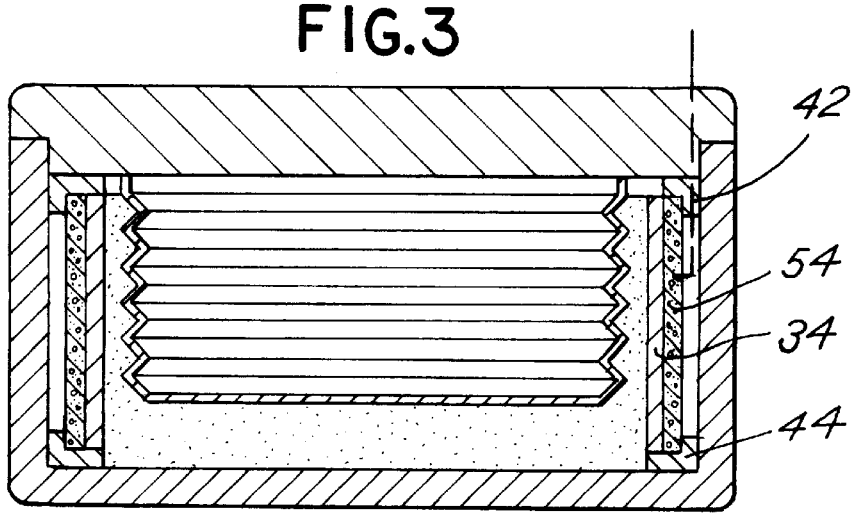
FIG. 3 is a cross-section of a delivery device incorporating a volume sensing device according to yet another preferred embodiment of the invention.

FIG. 2 illustrates an alternative embodiment according to the present invention. Bellows 22 is provided with a recess 28 formed in its bottom surface 30. Disposed within recess 28 is a circular disc of absorbent material 50. Absorbent material 50 is retained by a screen 52 secured to the bottom surface 30 of bellows 22. Alternatively, screen 52 may be eliminated and absorbent material 50 secured to bottom surface 30 using suitable adhesive. FIG. 3 represents another embodiment of the invention in which absorbent material is provided in the form of an absorbent outer ring 54 which is disposed outside of member 34. In this embodiment, polyvinyl alcohol may again be employed as the absorbent material.

FIGS. 1–3 for clarity illustrate member 34 as being somewhat removed from the outer periphery of bellows 22. It should be noted that member 34 is preferably disposed more proximate bellows 22 than is illustrated and that the drawings are intended to illustrate the general orientation of elements of the preferred embodiments. It is preferable to provide member 34 in very close proximity or even in contact with the outer periphery of bellows 22 in order to maximize the capacitance formed between bellows 22 and member 34. Those of ordinary skill will recognize that a constant capacitance will exist between the outer surface of member 34 and the inner surface of pump housing side wall 18. Thus, the variable capacitor provided by bellows 22 and member 34 will be in parallel with the capacitor formed by member 34 and side wall 12. Maximizing the capacitive effects created between bellows 22 and member 34 while minimizing the capacitive effects of the constant capacitance between bellows 22 and side wall 18 will therefore result in increased volume sensing capability.

Figure 4:
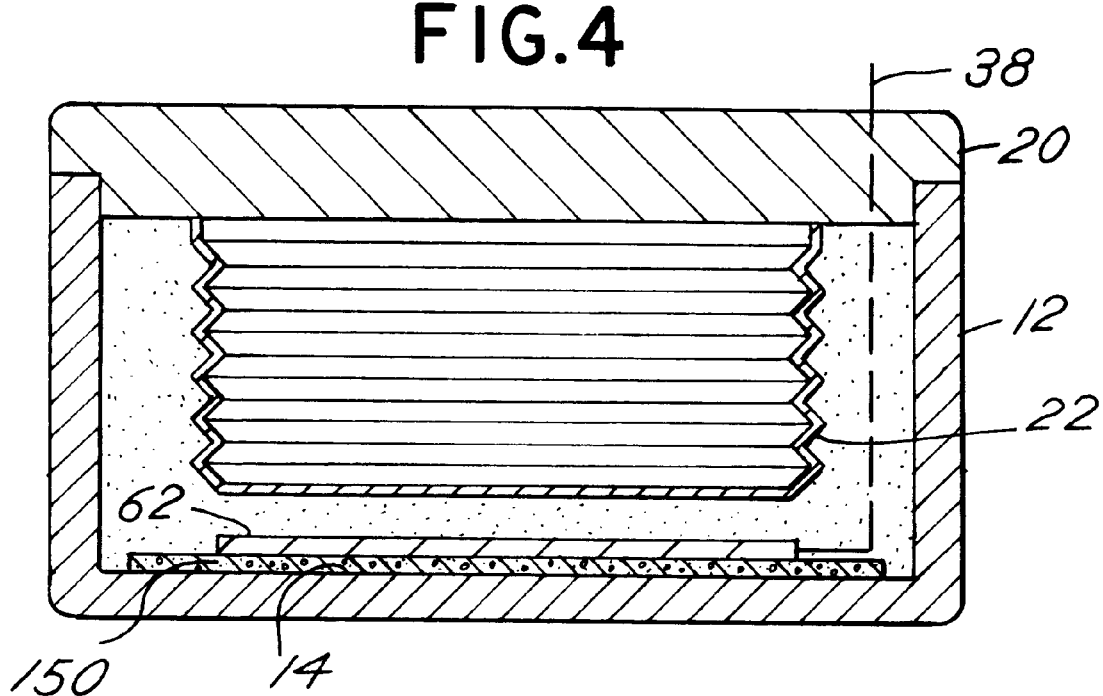
FIG. 4 is a cross-section of a delivery device incorporating a volume sensing device according to still another preferred embodiment of the invention.
Figure 5:
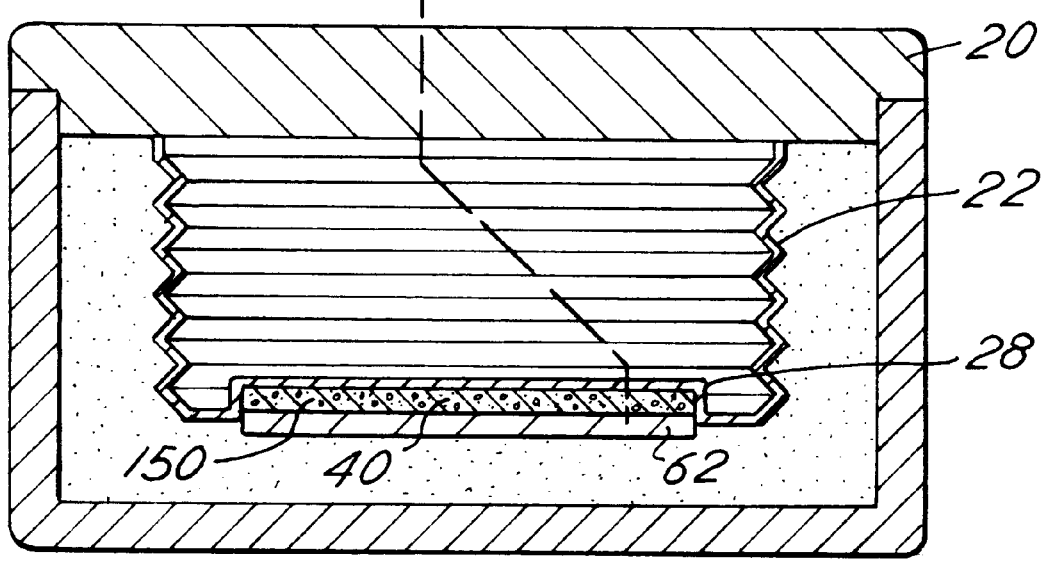
FIG. 5 is a cross-section of a delivery device incorporating a volume sensing device according to another preferred embodiment of the invention.

Referring now to FIGS. 4 and 5, another aspect of the invention is embodied in a solid-state variable capacitor housed within the pump housing 12. This aspect of the invention recognizes that, quite unexpectedly, absorbent material 150 may be employed as a dielectric having dielectric properties that vary according to the amount of propellant absorbed in the material. Referring to FIG. 4, absorbent material 150 is disposed between the housing bottom 14 and a conductive plate 62 which is preferably disc-shaped. Absorbent material 150 may be secured to the housing bottom 14 by suitable adhesive means. Similarly, conductive plate 62 may be adhesively secured to absorbent material 150. A feed through wire is electrically isolated from the pump common voltage and communicates the charge on plate 62 to the pump exterior for capacitance measurement readings relative to the pump common voltage, for example, measured at bulkhead 20. Housing bottom 14 and conductive plate 62 are preferably constructed of titanium and form first and second capacitor plates which "sandwich" the absorbent material 150.

In operation, the propellant contained within the pump housing exists in both liquid and vapor phases. Absorbent material 150 is preferably a polyvinyl alcohol sponge whose absorption is sufficient to absorb all of the liquid phase of the propellant. In operation, the vapor phase of the propellant maintains a substantially constant pressure on the exterior of bellows 22 and as the drug supply in bellows 22 depletes, bellows 22 will gradually collapse towards its empty position. As a consequence of the bellows collapse, the volume occupied by the propellant will increase and some of the liquid phase of the propellant will evaporate to occupy the increased volume. As a consequence of this evaporation, absorbent material 150 will "dry out" to some extent and the dielectric properties of the combination of the absorbent material and the absorbed liquid propellant will change. Thus, the capacitance between the bellows housing 14 and the conductive plate 62 will change as the volume of bellows reservoir changes. Notably, with regard to the components that make up the capacitor, there are no moving parts to affect the variation in capacitance.

Still referring to FIG. 4, the invention also contemplates employing bellows 22 in conjunction with conductive plate 62 as a switch closure to indicate a full bellows. In such a configuration, the full position of bellows 22 would coincide with electrical contact between the bottom surface of bellows 22 and conductive plate 62. Such a device would provide positive indication of a full bellows condition.

FIG. 5 illustrates another preferred embodiment of the solid-state variable capacitor according to the present invention. Here, absorbent material 150 and conductive plate 62 are disposed within a recess 28 in bellows 22. Conductive plate 62 is preferably provided with apertures or as a screen to permit absorption of the liquid propellant. In this embodiment, feed through wire 38 is secured to conductive plate 62. Insulation (not shown) on feed through wire 38 provides electrical isolation from the exterior of bellows 22 and bulkhead 20.

Certain advantages provided by the invention will be recognized from the foregoing description. First, the invention provides volume-sensing capabilities without adding to the pump volume or dimensions since the component parts of the capacitor according to the invention may be incorporated within existing pump configurations. Second, the volume-sensing capabilities may be provided without inhibiting the compatibility of the pump with MRI equipment—no magnetic components are employed. Still further, the sensing capabilities provided by the invention are not affected by asymmetrical bellows positioning. The capacitance between the conductive ring and bellows surface is not affected by asymmetrical bellows positioning, for example, if the bottom surface of the bellows is not exactly parallel to the bottom of the pump housing. Similarly, the sensing capabilities of the solid-state variable capacitor provided by the invention is unaffected by variations in the symmetrical positioning of the bellows.

Those skilled in the art will recognize that the preferred embodiments may be altered or amended without departing from the true spirit and scope of the invention, as defined in the accompanying claims.

What is claimed is:

1. A drug delivery device comprising:
   a housing;
   an expansible reservoir within the housing for containing a supply of drug, the reservoir defining a volume;
   a propellant contained in the housing as both a liquid phase and a vapor phase so as to maintain a substantially constant vapor pressure force on the reservoir as the reservoir volume changes;
   a capacitor disposed within the housing, the capacitor having a capacitance and comprising an absorbent dielectric for absorbing the liquid phase of the propellant and having dielectric properties that vary with the amount of absorbed liquid phase of the propellant, whereby the capacitance of the capacitor changes with variations in the reservoir volume.

2. The drug delivery device of claim 1, wherein the reservoir includes a first conductive surface, the delivery device further comprising a second conductive surface, electrically isolated from the housing and disposed proximate the first conductive surface.

3. The drug delivery device of claim 2, wherein the second conductive surface is provided on a conductive flex circuit surrounding the reservoir.

4. The drug delivery device of claim 2, wherein the second conductive surface is provided on a ring surrounding the reservoir.

5. The drug delivery device of claim 4, wherein the ring is supported within the housing by an insulating spacer.

6. The drug delivery device of claim 1, wherein the absorbent dielectric is comprised of a material selected from the group consisting of polyvinyl alchohol, felt and cellulose.

7. The drug delivery device of claim 6, wherein the absorbent material is provided in the form of a disk secured to the bellows.

8. The drug delivery device of claim 1, wherein the absorbent dielectric is provided in the form of a ring surrounding the reservoir.

9. The drug delivery device of claim 1, wherein the absorbent dielectric is disposed between a bottom surface of the reservoir and a second plate affixed to the reservoir.

10. The drug delivery device of claim 1, wherein the absorbent dielectric is disposed between a first conductive plate and a top surface of a bottom of the housing.

11. An implantable pump having a volume sensor comprising:
    a pump housing;
    a bulkhead for sealing the pump housing and defining an inner chamber therewith;

an expandable bellows disposed within the chamber for containing a supply of drug, the bellows movable from a full expanded position to a collapsed empty position;

a capacitor disposed within the pump housing for providing a capacitance, the capacitor comprising an absorbent dielectric for absorbing the liquid phase of the propellant and having dielectric properties that vary with the amount of absorbed liquid phase of the propellant, whereby the capacitance of the capacitor changes with variations in the reservoir volume.

12. The implantable pump of claim 11, wherein the absorbent dielectric is disposed between a bottom surface of the reservoir and a second plate affixed to the reservoir.

13. The implantable pump of claim 11, further comprising a conductive surface disposed proximate the bellows, wherein the capacitor is formed by the bellows and the conductive surface.

14. The implantable pump of claim 13, wherein the conductive surface is provided on a ring surrounding the bellows.

15. The implantable pump of claim 14, wherein the ring is supported within the housing by an insulating spacer.

16. The implantable pump of claim 11, wherein the absorbent dielectric is comprised of a material selected from the group consisting of polyvinyl alchohol, felt and cellulose.

17. The implantable pump of claim 11, wherein the absorbent dielectric is provided in the form of a ring surrounding the bellows.

18. The implantable pump of claim 11, wherein the absorbent dielectric is disposed between a first conductive plate and a top surface of a bottom of the housing.

19. In an infusion pump having an expansible reservoir for containing a supply of drug and having a propellant having a liquid phase and a vapor phase for providing a substantially constant vapor pressure on the reservoir, a method of determining the volume of drug contained in the reservoir, the method comprising:

providing a capacitor comprising an absorbent dielectric for absorbing the liquid phase of the propellant and having dielectric properties that vary with the amount of absorbed liquid phase of the propellant, whereby the capacitance of the capacitor changes with variations in the reservoir volume; and determining changes in the volume of drug in the infusion pump by detecting changes in the measured capacitance.

20. The method of claim 19, wherein providing a capacitor further comprises providing a solid-state capacitor.

21. The method of claim 19, further wherein providing a capacitor further comprises providing as a dielectric a material selected from the group consisting of polyvinyl alchohol, felt and cellulose.

22. A drug delivery device comprising:

a housing;

an expandable reservoir within the housing for containing a supply of drug;

a capacitor disposed within the housing for providing a capacitance that varies as the reservoir moves, wherein the reservoir includes a first conductive surface, the delivery device further comprising a second conductive surface, electrically isolated from the housing and disposed proximate the first conductive surface, wherein the second conductive surface is provided on a ring surrounding the reservoir.

23. The drug delivery device of claim 22, wherein the ring is supported within the housing by an insulating spacer.

24. A drug delivery device comprising:

a housing;

an expandable reservoir within the housing for containing a supply of drug;

a capacitor disposed within the housing for providing a capacitance that varies as the reservoir moves, wherein the reservoir includes a first conductive surface, the delivery device further comprising a second conductive surface, electrically isolated from the housing and disposed proximate the first conductive surface, wherein the second conductive surface is provided on a conductive flex circuit surrounding the reservoir.

25. A drug delivery device comprising:

a housing;

an expandable reservoir within the housing for containing a supply of drug;

a capacitor disposed within the housing for providing a capacitance that varies as the reservoir moves;

a propellant for providing a propelling force on the reservoir;

an absorbent material for absorbing a liquid phase of the propellant, wherein the absorbent material is provided in the form of a ring surrounding the reservoir.

26. A drug delivery device comprising:

a housing;

an expandable reservoir within the housing for containing a supply of drug;

a capacitor disposed within the housing for providing a capacitance that varies as the reservoir moves;

a propellant for providing a propelling force on the reservoir;

an absorbent material for absorbing a liquid phase of the propellant, wherein the absorbent material is provided in the form of a disk secured to the reservoir.

27. An implantable pump having a volume sensor comprising:

a pump housing;

a bulkhead for sealing the pump housing and defining an inner chamber therewith;

an expandable bellows disposed within the chamber for containing a supply of drug, the bellows movable from a full expanded position to a collapsed empty position; and a capacitor disposed within the pump housing for providing a capacitance that varies with the position of the bellows, further comprising a conductive surface disposed proximate the bellows, wherein the capacitor is formed by the bellows and the conductive surface, wherein the conductive surface is provided on a ring surrounding the bellows.

28. The implantable pump of claim 27, wherein the ring is supported in the housing by an insulating spacer.

29. The implantable pump of claim 27, further comprising an absorbent material that is capable of absorbing propellant liquid within the housing.

30. The implantable pump of claim 29, wherein the absorbent material is provided in the form of a ring surrounding the bellows.

31. A drug delivery device comprising:

a housing;

an collapsible reservoir within the housing for containing a supply of drug;

a propellant contained in the housing, the propellant occupying the housing in both a liquid phase and a gaseous phase, the liquid phase evaporating into the gaseous phase to exert a substantially constant vapor pressure force on the reservoir;

a solid-state capacitor disposed within the housing, the solid-state capacitor including a first plate, a second plate in fixed relation to the first plate, and a dielectric material adapted to absorb the liquid phase of the propellant and disposed between the first and second plates, the capacitor thereby having a capacitance that varies with the amount of absorbed liquid phase of the propellant, whereby the capacitance of the capacitor changes with variations in the reservoir volume.

* * * * *